(12) United States Patent
Giles et al.

(10) Patent No.: US 10,446,381 B2
(45) Date of Patent: *Oct. 15, 2019

(54) ION ENTRY/EXIT DEVICE

(71) Applicant: Micromass UK Limited, Wilmslow (GB)

(72) Inventors: Kevin Giles, Stockport (GB); David J. Langridge, Macclesfield (GB); Jason Lee Wildgoose, Stockport (GB)

(73) Assignee: Micromass UK Limited, Wilmslow, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,298

(22) Filed: May 15, 2018

(65) Prior Publication Data

US 2018/0337030 A1  Nov. 22, 2018

Related U.S. Application Data

(63) Continuation of application No. 15/303,433, filed as application No. PCT/GB2015/051109 on Apr. 13, 2015, now Pat. No. 9,984,861.

(30) Foreign Application Priority Data

Apr. 11, 2014 (EP) ..................................... 14164500
Apr. 11, 2014 (GB) ................................... 1406575.9

(51) Int. Cl.
*H01J 49/06* (2006.01)
*G01N 27/62* (2006.01)
(Continued)

(52) U.S. Cl.
CPC .......... *H01J 49/061* (2013.01); *G01N 27/622* (2013.01); *H01J 49/0031* (2013.01); *H01J 49/422* (2013.01); *H01J 49/408* (2013.01)

(58) Field of Classification Search
CPC .... H01J 39/061; H01J 39/062; H01J 39/0031; G01N 27/622
See application file for complete search history.

(56) References Cited

U.S. PATENT DOCUMENTS

2009/0173880 A1* 7/2009 Bateman ............... H01J 49/065
250/292
2014/0048702 A1 2/2014 Green et al.

FOREIGN PATENT DOCUMENTS

WO 2013/093513 A1 6/2013

OTHER PUBLICATIONS

First Office Action for DE Patent Application No. 11 2015 001 770.4, dated Mar. 24, 2019.

* cited by examiner

*Primary Examiner* — Eliza W Osenbaugh-Stewart

(57) ABSTRACT

A method of introducing and ejecting ions from an ion entry/exit device (4) is disclosed. The ion entry/exit device (4) has at least two arrays of electrodes (20,22). The device is operated in a first mode wherein DC potentials are successively applied to successive electrodes of at least one of the electrode arrays ((20,22) in a first direction such that a potential barrier moves along the at least one array in the first direction and drives ions into and/or out of the device in the first direction. The device is also operated in a second mode, wherein DC potentials are successively applied to successive electrodes of at least one of the electrode arrays (20,22) in a second, different direction such that a potential barrier moves along the array in the second direction and drives ions into and/or out of the device in the second direction. The device provides a single, relatively simple device for manipulating ions in multiple directions. For example, the device may be used to load ions into or eject ions from an ion mobility separator in a first direction, and
(Continued)

may then be used to cause ions to move through the ion mobility separator in the second direction so as to cause the ions to separate.

17 Claims, 9 Drawing Sheets

(51) Int. Cl.
*H01J 49/00* (2006.01)
*H01J 49/42* (2006.01)
*H01J 49/40* (2006.01)

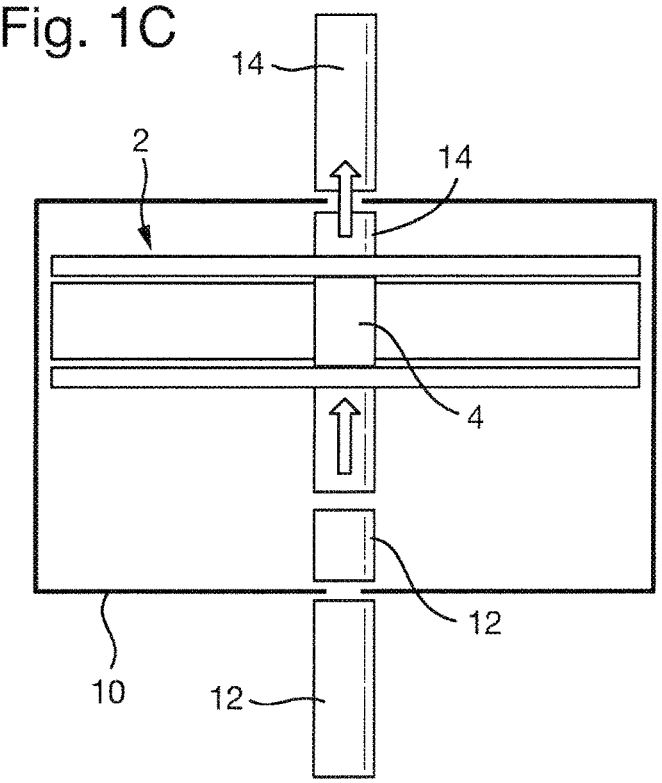
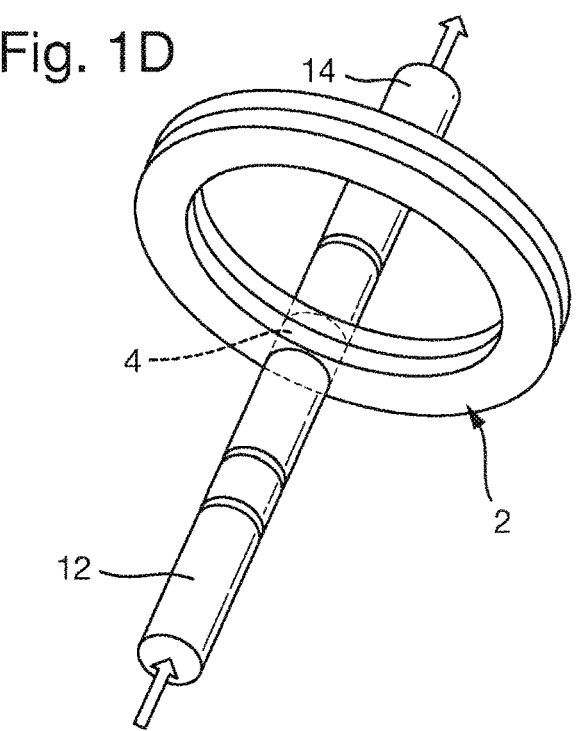

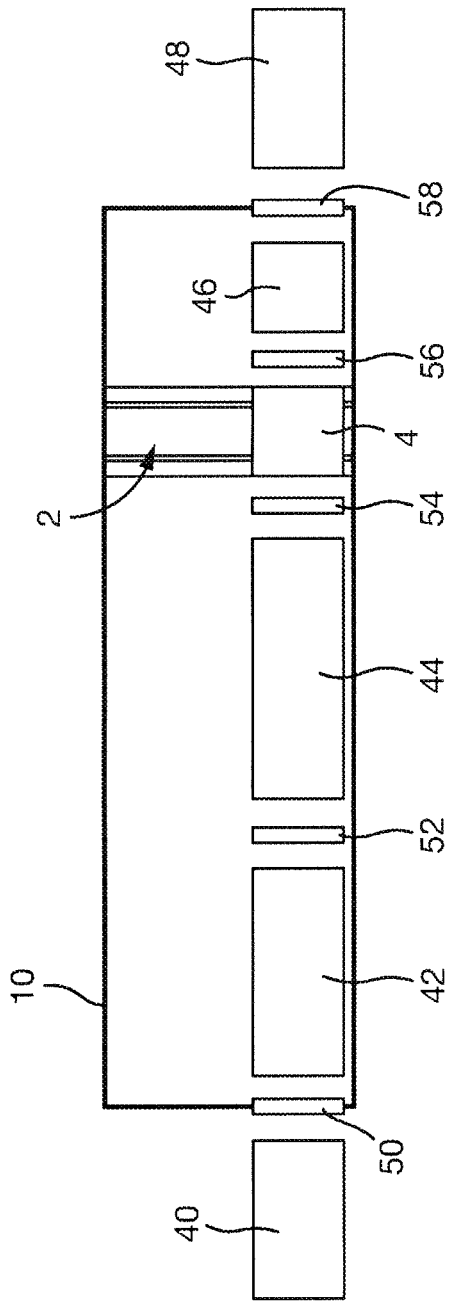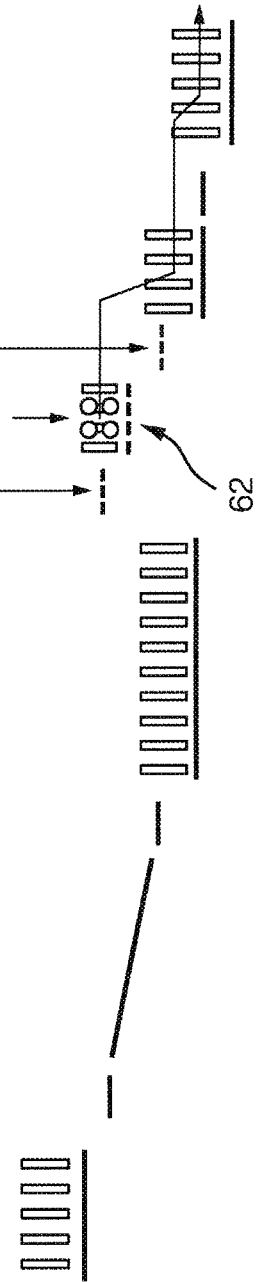

ION ENTRY/EXIT DEVICE

CROSS-REFERENCE TO RELATED APPLICATION

This application is a continuation of U.S. patent application Ser. No. 15/303,433, filed on Oct. 11, 2016, which is a national phase filing claiming the benefit of and priority to International Patent Application No. PCT/GB2015/051109, filed on Apr. 13, 2015, which claims priority from and the benefit of United Kingdom patent application No. 1406575.9 filed on Apr. 11, 2014 and European patent application No. 14164500.2 filed on Apr. 11, 2014. The entire contents of these applications are incorporated herein by reference.

BACKGROUND TO THE PRESENT INVENTION

Existing ion mobility separators generally operate in-line with the ion optical path of a mass spectrometer and so have a direct impact on the overall length of the instrument and also must be transited even if ion mobility separation is not required, potentially making timing between rapidly changing ion signals and subsequent analysers more problematic. This becomes more problematic as the length of ion mobility separator is increased in order to increase the resolution of the device.

It is known to separate ions in closed-loop separators in order to overcome the problem of having to provide a relatively long device in order to obtain the required resolution. However, it is desired to provide an improved technique for introducing and extracting ions from such a device and also for causing ions to begin to move around such a device.

It is desired to provide an improved method of introducing and ejecting ions from an ion mobility separation device, an improved ion entry/exit device, and an improved mass spectrometer or ion mobility spectrometer.

SUMMARY OF THE PRESENT INVENTION

From a first aspect, the present invention provides a method of introducing and ejecting ions from an ion mobility separation device, said method comprising:

providing an ion entry/exit device having at least two arrays of electrodes;

operating the device in a first mode, wherein DC potentials are successively applied to successive electrodes of at least one of the electrode arrays in a first direction such that a potential barrier moves along the at least one array in the first direction and drives ions into and/or out of the device in the first direction; and operating the device in a second mode, wherein DC potentials are successively applied to successive electrodes of at least one of the electrode arrays in a second, different direction such that a potential barrier moves along the at least one array in the second direction and drives ions into and/or out of the device in the second direction.

The present invention provides a single, relatively simple device for manipulating ions in multiple directions. For example, the device may be used to load ions into or eject ions from an ion mobility separator in a first direction, and may then be used to cause ions to move through the ion mobility separator in the second direction so as to cause the ions to separate. The device may also be used to bypass the separator in the first direction. This removes the need for multiple regions to manipulate ions.

The at least two arrays of electrodes may be arranged parallel to each other.

Both of said arrays may be simultaneously operated in either said first or second modes. Alternatively, only one of said arrays may be operated in the first mode and only one other array may be operated in the second mode.

Each array of electrodes may comprise a plurality of electrodes arranged in rows and columns. Each row may comprise x electrodes, wherein x is selected from the group consisting of: >3; >4; >5; >6; >7; >8; >9; >10; >15; >20; >25; >30; >35; >40; >45; and >50. Additionally, or alternatively, each column may comprise y electrodes, wherein y is selected from the group consisting of: >3; >4; >5; >6; >7; >8; >9; >10; >15; >20; >25; >30; >35; >40; >45; and >50. Any combination of number of electrodes per row and number of electrodes per column may be selected from the above lists.

Each array of electrodes may comprise a plurality of electrodes arranged in rows and columns. In said first mode said DC potentials may be applied to the electrodes in a first row and may then be successively applied to different rows of electrodes such that said potential barrier moves along the array in the first direction. Alternatively, or additionally, in said second mode said DC potentials may be applied to the electrodes in a first column and may then be successively applied to different columns of electrodes such that said potential barrier moves along the array in the second direction.

As described above, each array may have a plurality of electrodes arranged in each row and in each column. This arrangement is particularly advantageous wherein each array operates in both the first and second modes. Less preferably, one array operates in the first mode and another array operates in the second mode. In such an arrangement, one array may comprise only a column of electrodes arranged in the first direction for driving ions in the first direction in the first mode of operation, i.e. there is only one electrode in each row. Another array may comprise only a row of electrodes arranged in the second direction for driving ions in the second direction in the second mode of operation, i.e. there is only one electrode in each column.

The method may further comprise supplying RF voltages to said arrays of electrodes so as to confine ions in the direction between the arrays.

The same phase RF potential may be applied to all of the electrodes in the same column of electrodes, and adjacent columns of electrodes may be maintained at different RF phases, such as opposite RF phases. Alternatively, the same phase RF potential may be applied to all of the electrodes in the same row and adjacent rows of electrodes may be maintained at different RF phases, such as opposite RF phases.

The first direction and second directions may be orthogonal to each other. For example, the first and second directions may be aligned with the directions of the columns and rows respectively.

The method may be operated in the first mode so as to load ions into the device in the first direction, and the method may then be operated in said second mode so as to eject these ions from the device in the second direction.

The method may comprise temporally separating ions according to a physicochemical property prior to their entry into the ion entry/exit device; then receiving the ions in the ion entry/exit device; operating the ion entry/exit device in the first mode so that the temporally separated ions are ejected from the device in the first direction; and temporarily operating the ion entry/exit device in the second mode so as to selectively eject ions having a selected value, or range of values, of said physicochemical property from the device in the second direction. The physicochemical property may be mass to charge ratio or ion mobility.

The method may further comprise ejecting said ions from the ion entry/exit device into a first ion guide, ion trap or ion processing device in said first mode and into a second ion guide in the second mode.

The second ion guide may comprise electrodes and the method may comprise applying DC voltages to the electrodes of the second ion guide so as to drive ions along the longitudinal axis of the second ion guide; and wherein either a static DC potential gradient is applied along the axial length of the second ion guide so as to drive ions along said longitudinal axis; or wherein one or more DC potentials is applied to successive electrodes along the axial length of the second ion guide such that a DC potential barrier travels along the length of the second ion guide and drives ions along the second ion guide.

The second ion guide may be a closed-loop ion guide that starts and ends with said ion entry/exit device such that in the second mode ions are driven out of the ion entry/exit device through an exit aperture, pass around the closed-loop ion guide and are then reintroduced back into the ion entry/exit device through an entrance aperture.

The second mode of operation may continue to operate such that the potential barrier in the ion entry/exit region moves in the second direction and urges the reintroduced ions out of the ion entry/exit device in the second direction again so that the ions and pass around the ion guiding region again.

The ions may be caused to pass around the ion guide and through the ion entry/exit region a plurality of times, and as many times as desired. For example, the ions may pass around the second ion guide and through the ion entry/exit region ≥x times, wherein x is 2, 3, 4, 5, 6, 7, 8, 9, 10, 15 or 20.

A DC potential may be travelled around the second ion guide so as to drive ions from the exit aperture of the ion entry/exit device to the entrance aperture of the ion entry/exit device, and this travelling DC potential may be synchronised with the travelling DC potential present in the ion entry/exit device in the second mode of operation such that a travelling DC potential travels substantially continuously around the second ion guide and through the ion entry/exit device.

The travelling DC potential may travel substantially continuously around the second ion guide and through the ion entry/exit device at a constant speed.

The ion entry/exit device and/or second ion guide may form an ion mobility separator in which the ions separate along the longitudinal axis according to their ion mobilities.

The ion entry/exit device may be operated in a mode so as to eject at least some of the separated ions out of the device in the first direction and into said first ion guide, ion trap, or ion processing device. Alternatively, one or more additional ion entry/exit devices having the construction described herein may be provided for ejecting at least some of the separated ions out of the second ion guide and into a first ion guide, ion trap, or ion processing device. Any one of these ion entry/exit devices may have the following features.

The ions may separate according to their ion mobilities as they pass along the second ion guide, and the ion entry/exit device may then be switched to the first mode so as to eject at least some of the separated ions out of the device in the first direction and into said first ion guide, ion trap, or ion processing device.

The ion entry/exit device may be temporarily switched from the second mode to the first mode such that only ions of a first ion mobility, or first range of ion mobilities, that have passed along the second ion guide are ejected out of the ion entry/exit device in the first direction, whilst other ions having a second ion mobility, or second range of ion mobilities, pass through the ion entry/exit device in the second direction such that they continue on to pass through the second ion guide again.

The selectively ejected ions may be stored, mass analysed, fragmented to form fragment ions, or reacted with ions or molecules to form product ions within said first ion guide, ion trap, or ion processing device.

The method may comprise reintroducing the selectively ejected ions, fragment ions or product ions into the ion entry/exit device whilst operating the device in the second mode such that the reintroduced ions pass into the second ion guide again.

The method may comprise operating the ion entry/exit device in the first mode of operation such that ions are transmitted into, through and out of the ion entry/exit device in the first direction and into the first ion guide or ion trap, without being passed into said second ion guide.

During said first mode, the method may comprise maintaining the potential of at least some of the electrodes in at least one of the electrode arrays at a DC potential that is lower than the DC potential of the electrodes in the adjacent portion(s) of the second ion guide, such that a DC potential barrier is provided between the ion entry/exit device and the second ion guide which prevents ions from exiting the ion entry/exit device and entering the second ion guide. Alternatively, or additionally, during said second mode, the method may comprise maintaining the potential of at least some of the electrodes in at least one of the electrode arrays at a DC potential that is substantially the same as the DC potential of the electrodes in the adjacent portion(s) of the second ion guide such that substantially no DC potential barrier is provided between the ion entry/exit device and the second ion guide so that ions can exit the ion entry/exit device and enter the second ion guide.

It is contemplated that the ion entry/exit device of the present invention may comprise only one array of electrodes.

Accordingly, from a second aspect the present invention provides a method of introducing and ejecting ions from an ion entry/exit device, said method comprising:

providing an ion entry/exit device having at least one array of electrodes;

operating the device in a first mode, wherein DC potentials are successively applied to successive electrodes of the electrode array in a first direction such that a potential barrier moves along the array in the first direction and drives ions into and/or out of the device in the first direction; and operating the device in a second mode, wherein DC potentials are successively applied to successive electrodes of the electrode array in a second, different direction such that a potential barrier moves along the array in the second direction and drives ions into and/or out of the device in the second direction.

The method according to the second aspect may operate in any manner described herein in relation to the first aspect of the present invention, except wherein only a single array of electrodes may be used.

Ions may be held against the single array by applying a force to the ions in a direction towards the array. This maintains the ions proximal to the array such that the potentials applied to the array are able to move the ions. The force may be applied, for example, by a DC potential, an RF pseudo-potential or a gas flow.

The present invention also provides a method of mass spectrometry and/or ion mobility spectrometry comprising a method as described herein. The method may further comprise detecting the ions, mass analysing the ions or ion mobility analysing the ions.

The present invention also provides a method of mass spectrometry or ion mobility spectrometry comprising:

providing a closed loop ion guide having an ion entry/exit region arranged therein, wherein the ion entry/exit region comprises at least two arrays of electrodes;

operating the ion entry/exit region in a first mode, wherein DC potentials are successively applied to successive electrodes of at least one of the electrode arrays in a first direction such that a potential barrier moves along the at least one array in the first direction and drives ions into and/or out of the closed loop ion guide in the first direction; and operating the ion entry/exit region in a second mode, wherein DC potentials are successively applied to successive electrodes of at least one of the electrode arrays in a second, different direction such that a potential barrier moves along the at least one array in the second direction and drives ions around the longitudinal axis of the closed loop ion guide, and wherein the ions separate according to their ion mobilities as they pass around the closed loop ion guide.

This method may have any one or combination of the optional or preferred features described herein in relation to the first aspect of the present invention.

The first aspect of the present invention also provides an ion entry/exit device for a mass spectrometer and/or ion mobility spectrometer, said device comprising:

at least two arrays of electrodes;

at least one DC voltage supply; and control means for varying the electrical potentials applied to the electrodes of said at least two arrays with time;

wherein in a first mode of operation said control means successively applies DC potentials to successive electrodes of at least one of the electrode arrays in a first direction such that a potential barrier moves along the at least one array in the first direction for driving ions into and/or out of the device in the first direction; and wherein in a second mode of operation said control means successively applies DC potentials to successive electrodes of at least one of the electrode arrays in a second, different direction such that a potential barrier moves along the at least one array in the second direction for driving ions into and/or out of the device in the second direction.

The device may be arranged and configured to perform any of the methods described herein.

The second aspect the present invention also provides an ion entry/exit device for a mass spectrometer and/or ion mobility spectrometer, said device comprising:

at least one array of electrodes;

at least one DC voltage supply; and control means for varying the electrical potentials applied to the electrodes of said at least one array with time;

wherein in a first mode of operation said control means successively applies DC potentials to successive electrodes of the at least one array in a first direction such that a potential barrier moves along the at least one array in the first direction for driving ions into and/or out of the device in the first direction; and wherein in a second mode of operation said control means successively applies DC potentials to successive electrodes of the at least one array in a second, different direction such that a potential barrier moves along the at least one array in the second direction for driving ions into and/or out of the device in the second direction.

The present invention also provides a closed loop ion guide comprising an ion entry/exit device, wherein said ion entry/exit device comprises:

at least two arrays of electrodes;

at least one DC voltage supply; and control means for varying the electrical potentials applied to the electrodes of said at least two arrays with time;

wherein in a first mode of operation said control means successively applies DC potentials to successive electrodes of at least one of the electrode arrays in a first direction such that a potential barrier moves along the at least one array in the first direction for driving ions into and/or out of the closed loop ion guide in the first direction; and wherein in a second mode of operation said control means successively applies DC potentials to successive electrodes of at least one of the electrode arrays in a second, different direction such that a potential barrier moves along the at least one array in the second direction for driving ions around the longitudinal axis of the closed loop ion guide such that the ions separate according to their ion mobilities as they pass around the closed loop ion guide.

The present invention also provides a mass spectrometer and/or ion mobility spectrometer comprising an ion entry/exit device or closed loop ion guide as described herein.

The ion entry/exit device and/or closed loop ion guide and/or spectrometer may be configured so as to perform any one of the methods described herein.

The spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene reagent ions.

BRIEF DESCRIPTION OF THE DRAWINGS

Various embodiments of the present invention will now be described, by way of example only, and with reference to the accompanying drawings in which:

FIGS. 8A and 8B show the DC potentials applied to the spectrometer at a stage when the ions are ejected from the drift cell at the ion entry/exit device.

DETAILED DESCRIPTION OF PREFERRED EMBODIMENT

Figure 1A:
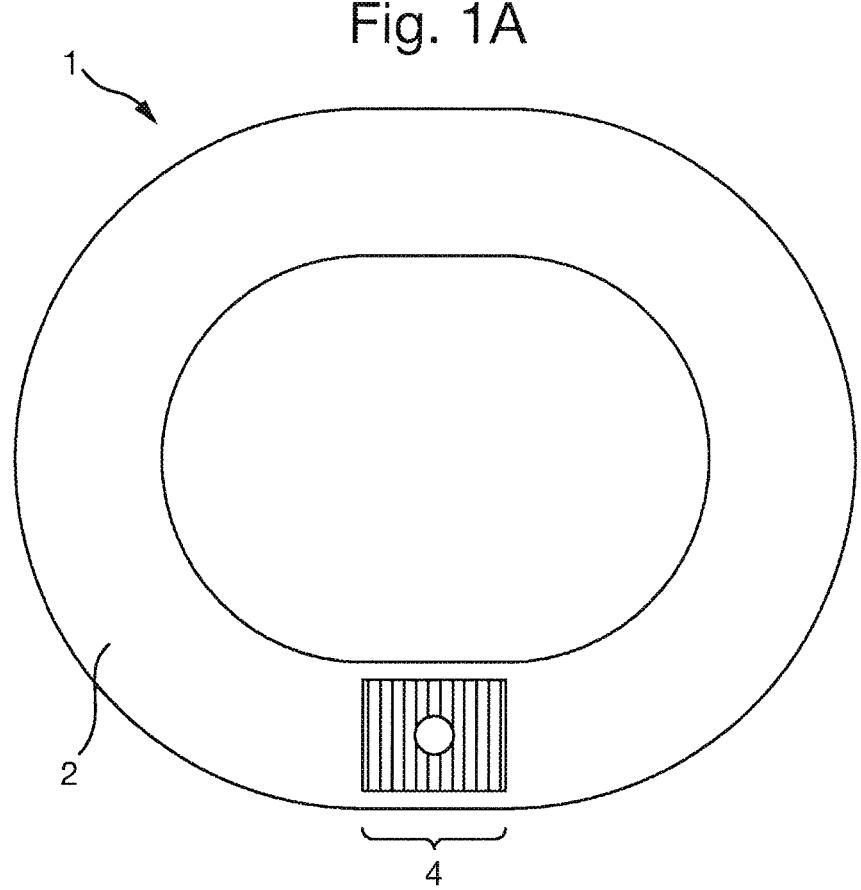
FIG. 1A shows a front view of a schematic of an ion mobility separator (IMS) according to a preferred embodiment of the present invention.

FIG. 1A shows a front view of a schematic of an ion mobility separator (IMS) according to a preferred embodiment of the present invention. The IMS device 1 comprises a closed-loop drift cell 2 around which the ions are guided in use. The drift cell 2 comprises a plurality of electrodes that act to confine the ions to an axial path that extends around the closed-loop drift cell 2. The drift cell 2 also comprises electrodes that urge the ions along the axial length of the drift cell. The ion guide is filled with a background gas such that as the ions are urged around the drift cell 2 they collide with the gas molecules and separate according to their ion mobilities through the gas. The ions may be urged around the closed-loop drift cell 2 once or multiple times before being extracted through an exit region 4. The ions may be urged around the drift cell 2 by applying one or more electrical potential that travels axially along the drift cell 2, or less preferably by a static DC potential gradient that is arranged axially along the drift cell 2.

Figure 1B:
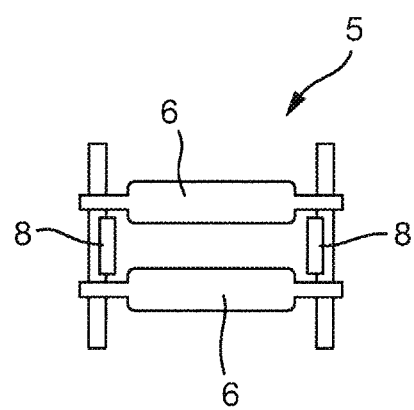
FIG. 1B shows a cross-sectional side view of a portion of the drift cell of the IMS device of FIG. 1A, and FIGS. 1C and 1D show different views of the embodiment of FIG. 1A.

FIG. 1B shows a cross-sectional side view of a portion of the drift cell 2 of the IMS device of FIG. 1A. FIG. 1B shows an embodiment of an electrode unit arrangement 5 that may be used to confine ions to the axis of the ion guiding path in the drift cell 2. At a given point along the axial length of the ion guiding path, the path is preferably defined between two RF electrodes 6 that are spaced apart in a first direction and two DC electrodes 8 that are spaced in a second, preferably orthogonal, direction. RF voltages are applied to the RF electrodes 6 so as to confine the ions between the RF electrodes 6, in the first direction. DC voltages are applied to the DC electrodes 8 so as to confine the ions between the DC electrodes 8, in the second direction. The electrode unit 5 is repeated along the axial length of the drift cell 2 such that ions are confined in the drift cell 2 at all points around the ion guide, except when ions are ejected from the ion entry/exit region 4, which will be described further below. The electrode units 5 are axially spaced along the ion guiding path and one of more DC potential may be successively applied to successive electrode units 5 such that a travelling DC potential travels around the drift cell 2 and hence forces the ions around the drift cell. Alternatively, different DC potentials may be applied to successive electrode units 5 around the ion guide such that a static DC gradient is applied along the axis that forces the ions around the drift cell 2.

The upper and lower sides of the drift cell 2 may be formed from printed circuit boards having the DC or RF electrodes 6,8 arranged thereon. Alternatively, or additionally, the radially inner and outer sides of the drift cell 2 may be formed from printed circuit boards having the RF or DC electrodes 6,8 arranged thereon.

FIG. 1C and FIG. 1D show an orthogonal view and a perspective view of the embodiment of FIG. 1A respectively. The drift cell 2 is arranged inside a chamber 10 that is filled with drift gas. Ions are guided into and out of the chamber 10 using RF ion guides 12,14. The RF ion guides 12,14 are also coupled with the ion entry/exit region 4 of the drift cell 2 such that ions can be guided into the drift cell 2 and out of the drift cell 2. In this embodiment, ions are guided into the chamber 10 and into the entry/exit region 4 of the drift cell 2 by input ion guides 12. If the ions are desired to be separated by their ion mobility then the ions are urged in an orthogonal direction to the ion entry direction and are urged around the oval or racetrack ion path of the drift cell 2. As the ions pass along the ion path they separate according to their ion mobility through the drift gas that is present in the chamber 10 and hence the drift cell 2. When ions are desired to be extracted from the drift cell 2 they are ejected in a direction towards the exit RF ion guides 14. The ions are then guided out of the chamber 10 by the exit ion guides 14.

On the other hand, if ion mobility separation of the ions is not required then ion species can be caused to pass from the input ion guide 12 to the output ion guide 14 directly through the entry/exit region 4 of the drift cell 2 and without passing around the drift cell 2. In other words, the drift cell 2 may be operated in a by-pass mode.

In a preferred mode of operation, it is possible to extract ions having a desired range of ions mobilities from the drift cell 2. This is achieved by causing ions to traverse around the drift cell 2 so that they separate and then synchronising the activation of one or more ejection voltages at the ion entry/exit region 4 with the time at which the ions of interest are at the entry/exit region 4. The desired ions are therefore ejected from the drift cell 2 and the other ion species remaining in the drift cell 2 can continue to pass through the drift cell 2 and separate according to ion mobility. Alternatively, the remaining ions may be discarded from the drift cell 2, for example, by removal of the RF voltages from the electrodes 6 such that the ions are no longer confined within the drift cell 2.

The ejected ions having the desired ion mobilities can be immediately transported away from the drift cell 2 to a mass analyser or detector. Alternatively, such ions may be trapped in a storage region whilst the next mobility cycle occurs in the drift cell 2 and until more ions of the same ion mobility range are ejected from the drift cell 2 into the storage region. After sufficient mobility cycles have been performed to accumulate the desired number of ions in the storage region, these ions may then be transported to an analyser for further analysis or to a detector. This method may be used to increase the ion signal of the desired ions. Additionally, or alternatively, the desired ions that have been ejected from the drift cell 2 may be fragmented, activated or dissociated and then reintroduced back into the drift cell such that the ion mobilities of the fragment, activated or product ions can be analysed by the drift cell 2.

Figure 2:
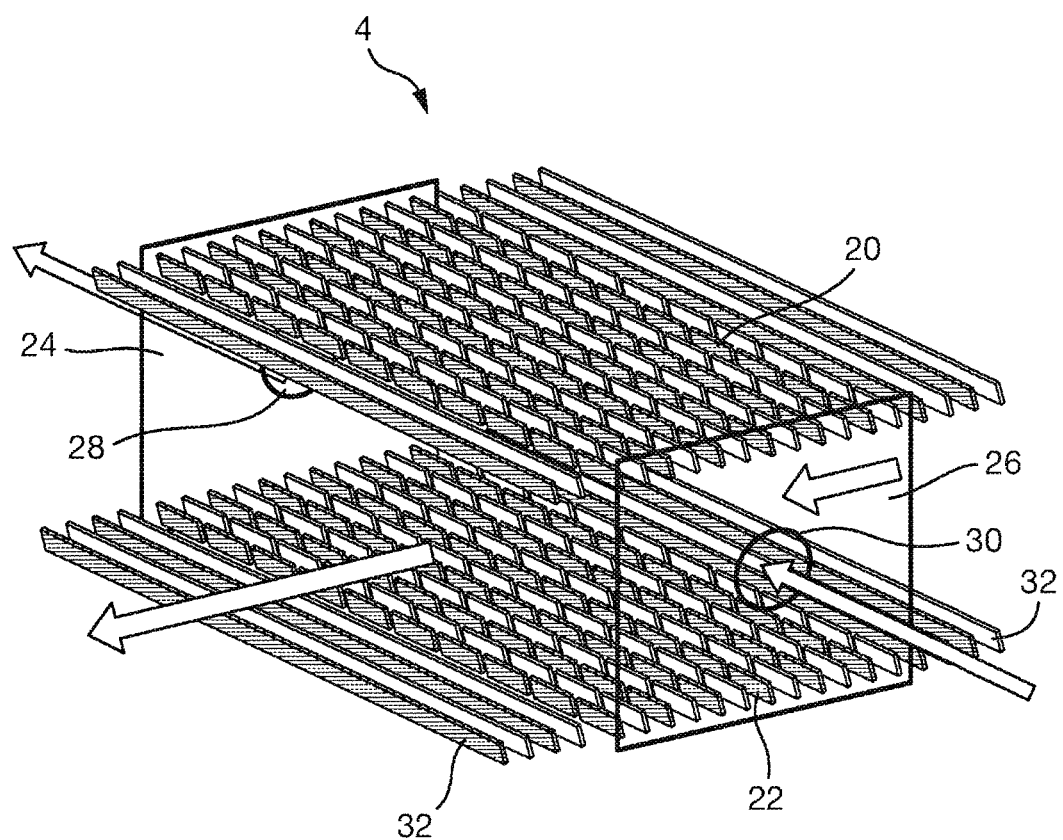
FIG. 2 shows a schematic perspective view of an embodiment of the ion entry/exit device of the drift cell.

FIG. 2 shows a schematic perspective view of an embodiment of the ion entry/exit device 4 of the drift cell 2. The ion entry/exit device 4 comprises two parallel, rectangular arrays of electrodes 20,22 that are spaced apart from each other. Each array of electrodes 20,22 comprises a plurality of electrodes arranged in rows and columns. Various electrical potentials are applied to these electrodes so as to manipulate the ions, as will be described in more detail below. The device has four sides that extend between the four edges of the arrays 20,22. Two of the opposing sides are formed by end plates 24,26, wherein each end plate has an orifice 28,30 therein. One of the end plates 26 has an ion injection orifice 30 for injecting ions into the device 4 from outside of the drift cell 2. The opposing end plate 24 has an ion ejection orifice 28 for ejecting ions out of the device 4 and the drift cell 2. The other two opposing sides are junctions with the drift electrodes 32 of the main drift cell 2. One of the junctions, the entrance junction, allows ions to pass into the device 4 from within another part of the drift cell 2. The other junction, the exit junction, allows ions to pass out of the device 4 and into another part of the drift cell 2.

RF electrical potentials are applied to the electrodes in the arrays of electrodes 20,22 in order to confine ions in the direction between the arrays 20,22. The same phase RF potential is preferably applied to all of the electrodes in the same column of electrodes (a column extends in the direction between the end plates 24,26 having orifices 28,30). Adjacent columns of electrodes are preferably maintained at different RF phases, preferably opposite RF phases. However, it is alternatively contemplated that same phase RF potential may be applied to all of the electrodes in the same row (a row extends in the direction parallel to the apertured plates 24,26). Adjacent rows of electrodes are preferably maintained at different RF phases, preferably opposite RF phases.

The ion entry/exit device 4 has plurality of modes of operation. According to a first mode of operation the device 4 is operated in a manner that injects or loads ions into the device 4 from outside of the drift cell 2. The device 4 may also be operated in another mode that urges ions out of the ion entry/exit device 4 into an adjacent part of the drift cell 2. The device 4 may also be operated in another mode which ejects ions out of the device 4 to a region outside of the drift cell 2. These modes will now be described with reference to FIGS. 3 and 4.

Figure 3:
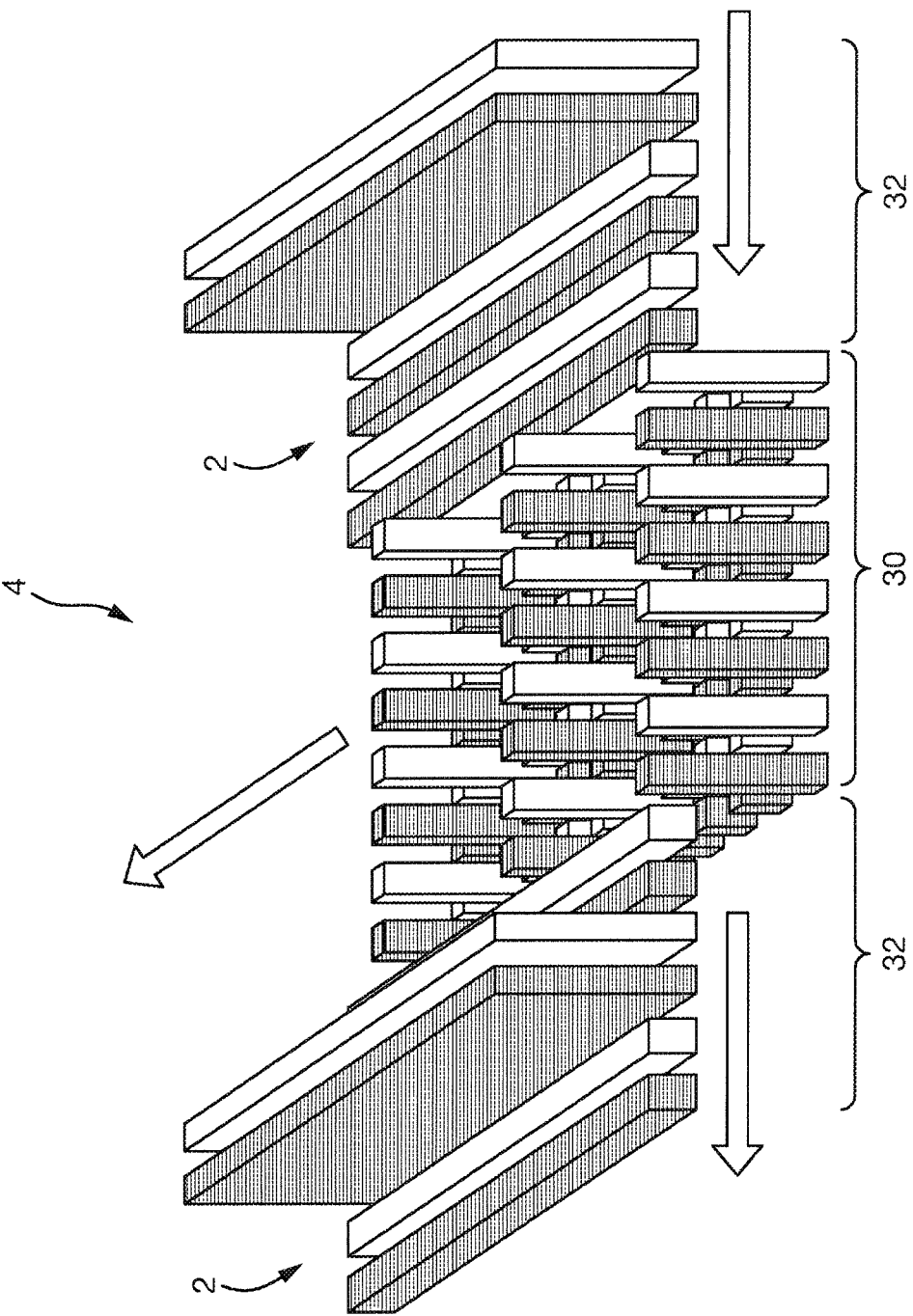
FIG. 3 shows a schematic of the electrical potentials that are applied to the ion entry/exit device during a mode in which ions are injected/loaded into the entry/exit device from outside of the drift cell.

FIG. 3 shows a schematic of the electrical potentials that are applied to the ion entry/exit device 4 and the adjacent parts of the drift cell 2 on either side of the device 4 during a mode in which ions are injected/loaded into the entry/exit device 4 from outside of the drift cell 2. The array of dark and light vertical bars 30 represent the potentials applied to either or both of the electrode arrays 20,22 in the ion entry/exit device 4. The colours of the vertical bars 30 represent the RF phases applied to the electrodes in the arrays 20,22, e.g. light coloured vertical bars represent one RF phase and dark coloured RF bars represent the opposite RF phase. The vertical heights of the vertical bars 30 represent the magnitudes of the DC voltages applied to the electrodes in the array(s) 20,22. It can be seen that relatively high amplitude DC potentials are applied to all of the electrodes in some of the rows of electrodes, and that relatively low amplitude DC potentials are applied to all of the electrodes in the adjacent rows of electrodes. During the mode in which ions are injected/loaded into the device 4, the DC potentials applied to the electrodes in the arrays 20,22 are varied with time such that the high DC voltages are successively applied to successive rows of electrodes in a direction from the ion injection orifice 30 towards the ion ejection orifice 28, and such that DC potential barriers travel in the direction from the ion injection orifice 30 towards the ion ejection orifice 28. Simultaneously, the low DC voltages are successively applied to successive rows of electrodes in a direction from the ion injection orifice 30 towards the ion ejection orifice 28. This causes ions to be forced into the ion entry/exit device 4 by the high amplitude DC voltages, wherein the ions travel in the regions of low DC voltages. The end plate having the exit orifice 28 may be maintained at a DC or RF potential such that ions are prevented from exiting the ion entry/exit device 4 during loading/injection of ions. Alternatively, or additionally, the amplitude of the high DC potentials may decrease as they travel in the direction towards the exit orifice 28. Alternatively, or additionally, a row of electrodes proximal to the exit orifice 28 may be maintained at high DC potentials so that the ions cannot be forced past this row and out of the ion entry/exit device 4 during loading.

The horizontally elongated bars 32 in FIG. 3 represent the potentials of electrodes in regions of the drift cell 2 that are adjacent to the ion entry/exit device 4. The colours of these horizontal bars represent the RF phases applied to the electrodes, e.g. light-coloured bars represent one RF phase and dark-coloured bars represent the opposite RF phase. The vertical heights at which the horizontally elongated bars 32 are located represent the magnitudes of the DC voltages applied to the electrodes. As can be seen, most of the horizontally elongated bars 32 are at a relatively low DC potential, but some of these bars are at a higher DC potential. These higher DC potentials are successively applied to successive electrodes along the axial length of the drift cell 2 so that a DC potential barrier travels along the axial length of the drift cell 2 and drives ions around the drift cell 2, which will be described in more detail in relation to FIG. 4.

Referring again to FIG. 3, the vertical heights at which the upper surfaces of the horizontally elongated bars 32 are located represent the magnitudes of the DC voltages applied to the electrodes. It can be seen that the magnitude of the low DC potentials applied to the electrode arrays 20,22 during ion loading/injection is smaller than the DC potentials at which the axially adjacent regions of the drift cell 2 is maintained. As such, the ions are prevented from passing from the ion entry/exit region 4 into the adjacent regions of the drift cell 2 during the ion loading/injection mode.

Once the ions have been loaded/injected into the ion entry/exit device 4, all of the electrodes in the array 20,22 may be maintained at the relatively low DC potential, i.e. there is no longer a need to drive ions in the direction between the end plates 24,26 having the orifices 28,30 and so the high DC potentials may be replaced by low DC potentials. The two end plates 24,26 may be maintained at DC or RF potentials that prevent ions from exiting through the end plates 24,26. The DC potentials applied to the electrodes in the arrays 20,22 may then be increased to the same value as the low DC potentials of the axially adjacent regions of the drift cell 2. There is then no DC barrier between the ion entry/exit region 4 and the axially adjacent portions of the drift cell 2. As such, ions may then pass easily from the ion entry/exit device 4 into the adjacent portion of the drift cell 2 so as to be separated according to their ion mobilities, as will be described with reference to FIG. 4.

Figure 4:
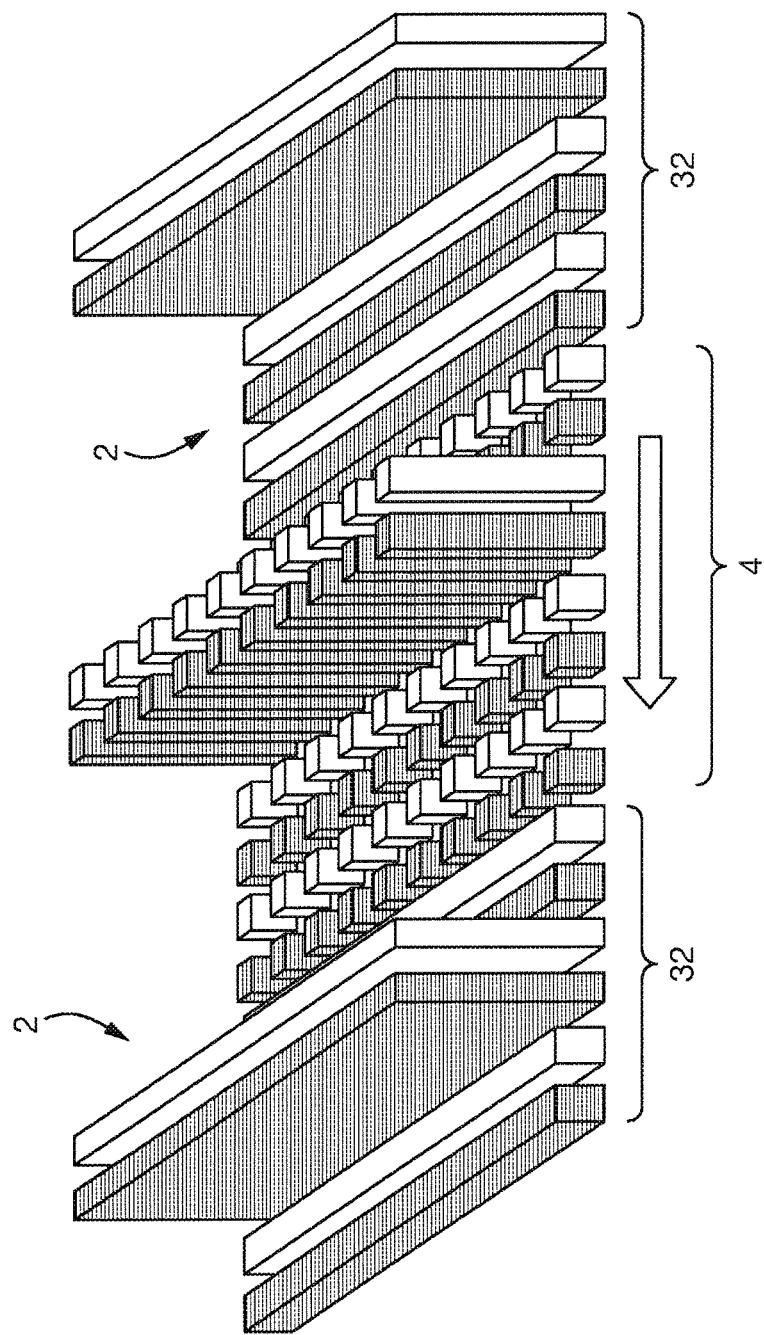
FIG. 4 shows the electrical potentials that are applied to the ion entry/exit device during a mode in which ions are driven out of the ion entry/exit region and into the adjacent part of the drift cell.

FIG. 4 shows the electrical potentials that are applied to the ion entry/exit device 4 and the axially adjacent parts of the drift cell 2 during a mode in which ions are driven out of the ion entry/exit region 4 and into the adjacent part of the drift cell 2. As described above, after ions have been loaded/injected into the ion entry/exit device 4 the DC potentials applied to the arrays of electrodes 20,22 are raised to correspond to the DC potentials of the adjacent parts of the drift cell 2. As such, there is no longer a DC barrier between the ion entry/exit device 4 and the adjacent parts of the drift cell. As shown in FIG. 4, the DC potentials applied to two columns of electrodes in the electrode arrays 20,22 are then increased to high DC voltages relative to the other electrodes in the arrays 20,22. These high DC voltages are successively applied to successive columns in the arrays 20,22 such that the high DC voltages move along the arrays in the axial direction of the drift cell 2, as indicated by the arrow in FIG. 4. This causes the ions to be driven out of the ion entry/exit device 4 and through the exit junction. The ions then pass into the axially adjacent portion of the drift region 2. The high DC voltages that drove the ions out of the ion entry/exit device 4 may then be successively applied to successive electrodes along the axial length of the remainder of the drift region 2 so as to continuously drive the ions around the entire drift region 2. Examples of such voltages are shown by the relatively high horizontally elongated bars in FIG. 4.

The ions are driven around the closed-loop drift cell 2 by the travelling DC voltages and back into the ion entry/exit device 4 through the entrance junction. The ions may be ejected from the drift cell 2 at this point, as will be described in more detail below. Alternatively, the ions may again be driven through the ion entry/exit device 4 by applying the travelling DC potentials to the columns of electrodes in the electrode arrays 20,22 and then driven around the drift cell 2 by the travelling DC potentials applied to the remainder of the drift cell electrodes. The ions may be driven around the drift cell 4 by this process as many times as is desired, until the ions have separated according to their ion mobility as desired. In this mode, the translation of the high DC potentials that drive ions through the ion entry/exit device 4 and into the axially adjacent part of the drift region 2 is preferably synchronised with the translation of the high DC potentials around the rest of the drift region. As such, the ion entry/exit region 4 is substantially ion-optically identical to the remainder of the drift region 2 during the mode of operation in which the ions are translated around the closed-loop drift cell a plurality of times.

When it is desired to eject ions from the drift cell, the DC potentials applied to the arrays of electrodes 20,22 in the ion entry/exit region 4 may be lowered again relative to the adjacent parts of the drift cell 2 as shown in FIG. 3. DC potentials may then be applied to the arrays of electrodes 20,22 so as to drive ions in the direction from the injection orifice 30 of the injection end plate 26 to the ejection orifice 28 of the ejection end plate 24. This is performed in the same manner as the ion loading/ejection mode of FIG. 3, except that in the ejection mode there is no potential barrier preventing the ions exiting the ion entry/exit device through the ejection orifice 30 of the ejection end plate 26. It will be appreciated that alternatively the ions could be ejected from the ion entry/exit device 4 through the same orifice 30 that they were loaded/injected by translating the high DC potentials in the opposite direction to the loading/injection direction.

The ion entry/exit region 4 may operate in a bypass mode in which ions are not desired to be driven around the closed-loop drift cell 2, and in which the ions are not caused to separate. This mode is the same as that described in relation to FIG. 3, except that the ions simply pass directly from the entrance orifice 30 and out of the exit orifice 28 without being transmitted orthogonally into the axially adjacent portion of the drift cell 2. The ions may be prevented from passing into the axially adjacent portion of the closed-loop drift cell 2 by the DC potentials on the electrodes arrays 20,22 being lower than those of the adjacent parts of the drift cell 2. The ions may or may not be driven through the ion entry/exit region 4 by the high DC potentials described in relation to FIG. 3.

Figure 5A:
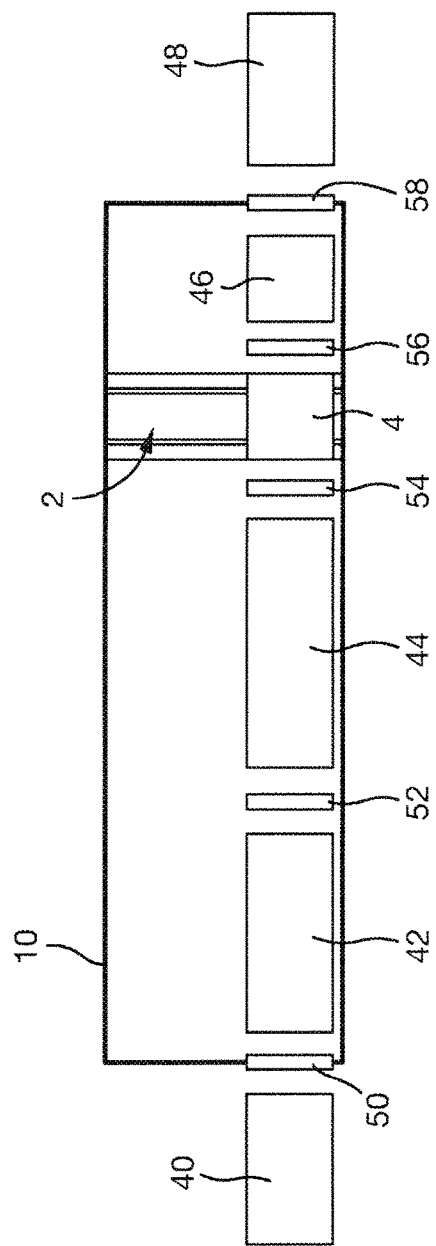
FIG. 5A shows a schematic of a preferred embodiment of a spectrometer comprising the IMS device.

FIG. 5A shows a schematic side view of a preferred embodiment of a spectrometer comprising the IMS device. The spectrometer comprises a drift gas chamber 10, an ion trap 40, a helium cell 42, an ion accumulation cell 44, the IMS device 2, an exit cell 46 and an ion transfer cell 48. Electrode gates 50-58 are arranged between the above described successive components. In particular, an entrance gate 54 is arranged upstream of the ion entry/exit device 4 and an exit gate 56 is arranged downstream of the ion entry/exit device 4. The IMS device 2 corresponds to that shown in FIG. 1C.

Figure 5B:
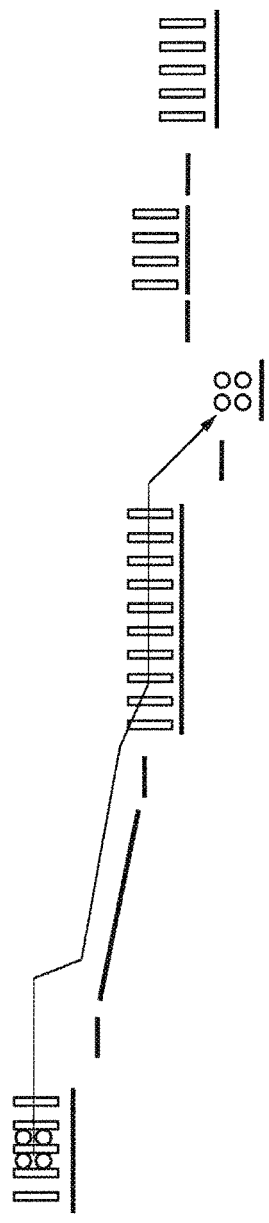
FIG. 5B shows a potential energy diagram of the DC potentials applied to the components of the spectrometer in a mode in which ions are being accumulated in the ion entry/exit device of the drift cell.

FIG. 5B shows a potential energy diagram of the DC potentials applied to the components of the spectrometer in a mode in which ions are being accumulated in the ion entry/exit device 4 of the drift cell 2. Ions are released from the ion trap 40 and are then driven through the helium cell 42 by an axial electric field. The ions then pass through the ion accumulation cell 44 and into the ion entry/exit device 4 through the ion entrance orifice 30 in the entrance end plate 26 described above in relation to FIG. 2. The DC potentials of the electrodes in the electrode arrays 20,22 of the ion entry/exit device 4 are maintained lower than the DC potentials applied to the accumulation cell 44, the entrance gate 54 and the exit gate 56. As such, ions are axially trapped and accumulate in the ion entry/exit device 4. The ions enter the ion entry/exit device 4 through the entrance orifice 30 of the entrance end plate 26 described above in relation to FIG. 2. A travelling DC wave may be applied to the rows of electrodes in the electrode arrays 20,22 in order to urge ions into the ion entry/exit device 4, as described with reference to FIG. 3. The DC potential of the IMS drift cell 2 (excluding the ion entry/exit device 4) is represented by the horizontal line that is parallel and vertically above the line representing the DC voltage applied to the arrays 20,22 of the ion entry/exit device 4. The potential difference represented by the gap between these two lines prevents ions from passing out of the ion entry/exit device 4 and into the axially adjacent parts of the IMS drift cell 2.

Figure 6A:
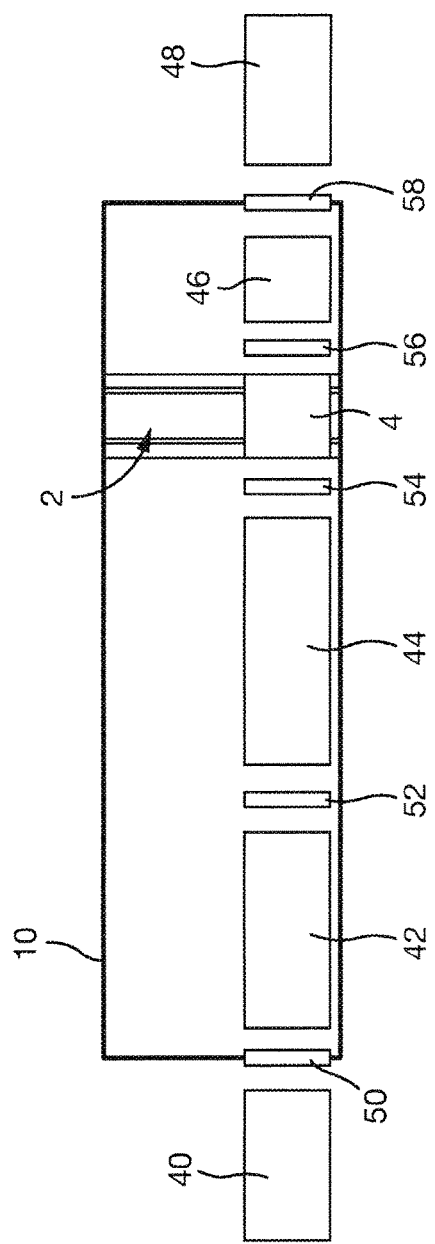
FIGS. 6A and 6B show how the potentials applied to the spectrometer are altered in preparation for moving ions from the ion entry/exit device into the axially adjacent part of the IMS drift cell.
Figure 6B:
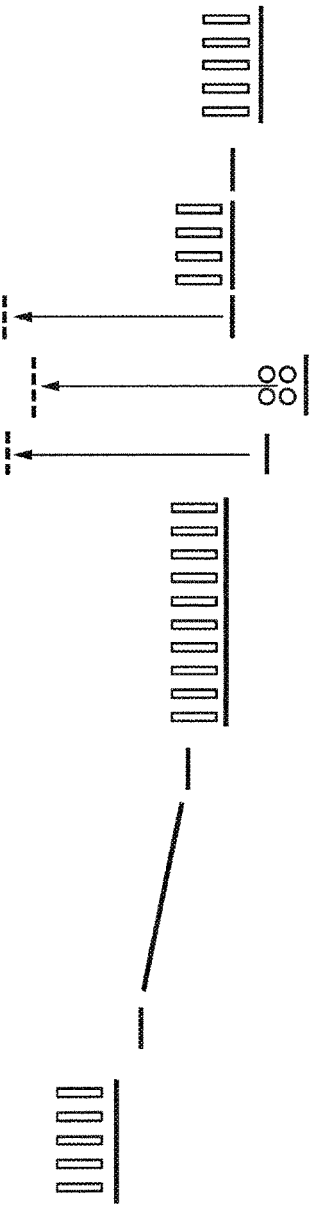

FIGS. 6A and 6B correspond to FIGS. 5A and 5B, except that they show how the potentials applied to the spectrometer are altered in preparation for moving ions from the ion entry/exit device 4 into the axially adjacent part of the IMS drift cell 2. As shown by the arrows in FIG. 6B, the DC potentials of the entrance gate 54, array electrodes 20,22 and exit gate 56 are raised to the DC potentials illustrated by the horizontal dashed lines. The DC potentials applied to the arrays of electrodes 20,22 are then equivalent to the DC potentials applied to the adjacent parts of the IMS drift cell 2, and hence there is no DC barrier preventing ions from passing from the ion entry/exit device 4 into the adjacent part of the IMS drift cell 2.

Figure 7A:
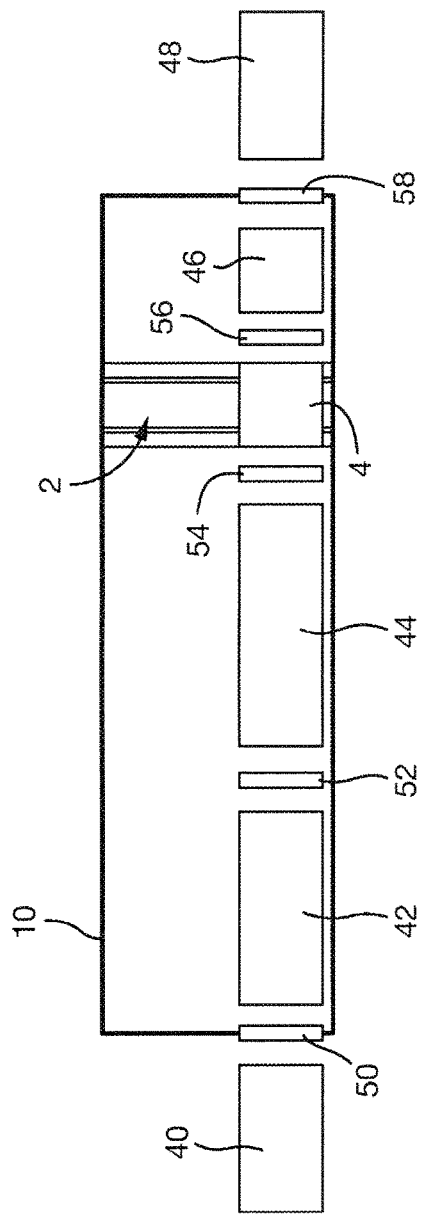
FIGS. 7A and 7B show the DC potentials applied to the spectrometer at a stage when the ions are driven out of the ion entry/exit device into the adjacent part of the IMS drift cell.
Figure 7B:
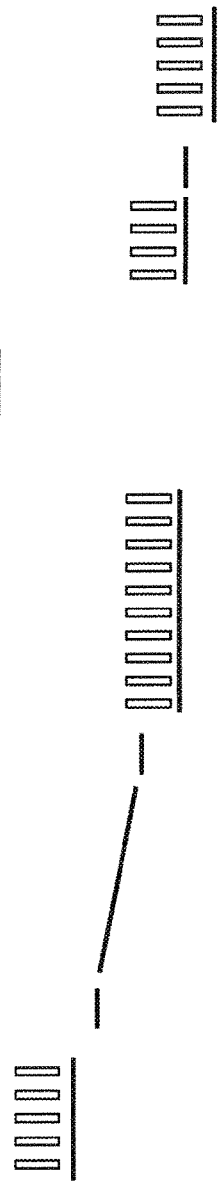

FIGS. 7A and 7B correspond to FIGS. 6A and 6B, except that they show the potentials at a stage when the ions are driven out of the ion entry/exit device 4 into the adjacent part of the IMS drift cell 2. As described above with reference to FIG. 4, the ions are driven out of the exit aperture 28 in the apertured exit plate 24 by applying DC travelling potentials to the columns of electrodes in the arrays of electrodes 20,22. These travelling potentials are illustrated by the series of parallel horizontal lines 60 in FIG. 7B. The ions are then driven around the drift cell 2 by travelling DC potentials such that the ions separate according to their ion mobilities, as has been described above. When the ions have passed around the drift cell 2 the desired number of times, the ions may be ejected at the ion entry/exit device 4. The length of time the potentials of the electrode arrays 20,22 are in the mode shown in FIG. 7B dictates how many passes the ions of given ion mobility make around drift cell 2.

FIGS. 8A and 8B correspond to FIGS. 7A and 7B, except that they show the DC potentials applied to the spectrometer at a stage when the ions are ejected from the drift cell 2 at the ion entry/exit device 4. As shown by the arrows in FIG. 8B, the DC potentials of the entrance gate 54, array electrodes 20,22 and exit gate 56 are lowered to the DC potentials illustrated by the horizontal dashed lines. The DC potentials of the entrance gate 54, array electrodes 20,22, exit gate 56, exit cell 45 and ion transfer cell 48 progressively decrease such that the ions are urged out of the ion entry/exit device 4 and along the spectrometer towards the ion transfer cell 48. The ions leave the ion entry/exit device 4 through the exit orifice 28 of the exit end plate 24 described above in relation to FIG. 2. A travelling DC wave is applied to the rows of electrodes in the electrode arrays 20,22 in order to urge ions out of the exit orifice 28. This is represented by the series of vertical lines 62 in the electrode array region of FIG. 8B.

Varying the potentials applied to the ion entry/exit device 4 relative to the remainder of the drift cell 2 during loading or ejection of ions at the ion entry/exit device 4 facilitates ion entry and exit from the drift cell 2 without having to alter the potentials of the other components of the spectrometer that are upstream or downstream. This also enables a bypass mode in which ions are not separated in the drift cell 2. For example, the DC potentials of the entrance gate 54, electrode arrays 20,22 and exit gate 56 may be made equivalent to the DC potentials of the accumulation cell 44 and exit cell 46 such that ions pass continuously from the accumulation cell 44, through the ion entry/exit device 4 and into the exit cell 46 without being separated in the drift cell 2.

The travelling DC waves applied to the drift cell 2 outside of the ion entry/exit device 4 may be operated continually during the above modes.

Although the present invention has been described with reference to preferred embodiments, it will be understood by those skilled in the art that various changes in form and detail may be made without departing from the scope of the invention as set forth in the accompanying claims.

For example, although travelling DC potentials have been described as being used for driving ions around the region of the drift cell 2 outside of the ion entry/exit device 4, static DC gradients may be used instead for this purpose.

It will be appreciated that drift cells 2 having continuous ion guiding paths of shapes other than circular or oval paths are also contemplated as being within the scope of the present invention.

The ion entry/exit device 4 may be used for manipulating ions in systems other than ion mobility drift cells 2. For example, the ion entry/exit device 4 may be used to inject ion into or eject ions from another type of device.

The drift cell 2 (or other type of device) need not be a closed-loop device around which ions are guided. For example, the ion entry/exit device 4 could be used in a linear device. The ions may pass along such a non-closed loop device once, or may be reflected along the device multiple times.

The geometry of the electrode arrays 20,22 may be varied and need not be arrays having columns and rows of electrodes.

The direction of the travelling DC potentials in the electrode arrays may be changed or may provide multiple directional travel options.

The invention claimed is:

1. An ion entry/exit device for a mass spectrometer and/or ion mobility spectrometer, said device comprising:
   at least two arrays of electrodes, wherein each array of electrodes comprises a plurality of electrodes arranged in rows and columns; and
   at least one DC voltage supply;
   wherein said at least one DC voltage supply is configured to:
   in a first mode of operation successively apply DC potentials to successive electrodes of at least one of the electrode arrays in a first direction such that a potential barrier moves along the at least one array in the first direction and drives ions into and/or out of the device in the first direction;
   wherein in said first mode said at least one DC voltage supply applies said DC potentials to the electrodes in a first row and then successively to different rows of electrodes such that said potential barrier moves along the array in the first direction; and/or
   wherein in a second mode of operation said at least one DC voltage supply applies DC potentials to the electrodes in a first column and then successively to different columns of electrodes such that a potential barrier moves along the array in a second, different direction.

2. The device of claim 1, wherein said at least two arrays of electrodes are arranged parallel to each other.

3. A method of introducing and ejecting ions from an ion mobility separation device comprising the ion entry/exit device of claim 1, said method comprising:
   operating the ion entry/exit device in said first mode, wherein DC potentials are successively applied to successive electrodes of at least one of the electrode arrays in a first direction such that a potential barrier moves along the at least one array in the first direction and drives ions into and/or out of the ion entry/exit device in the first direction;
   wherein in said first mode said DC potentials are applied to the electrodes in a first row and are then successively applied to different rows of electrodes such that said potential barrier moves along the array in the first direction; and/or
   operating the ion entry/exit device in said second mode, wherein in said second mode DC potentials are applied to the electrodes in a first column and are then successively applied to different columns of electrodes such that a potential barrier moves along the array in a second, different direction.

4. The method of claim 3, further comprising supplying RF voltages to said arrays of electrodes so as to confine ions in the direction between the arrays.

5. A mass spectrometer and/or ion mobility spectrometer comprising an ion entry/exit device as claimed in claim 1.

6. The device of claim 1, wherein said at least two arrays of electrodes are formed from printed circuit boards.

7. A method of introducing and ejecting ions from an ion mobility separation device, said method comprising:
   providing an ion entry/exit region having at least two arrays of electrodes; and
   operating the ion entry/exit region in a first mode, wherein DC potentials are successively applied to successive electrodes of at least one of the electrode arrays in a first direction such that a potential barrier moves along the at least one array in the first direction and drives ions into and/or out of the region in the first direction;
   wherein the method is operated in the first mode and ions are loaded into the region in the first direction, and the method is then operated in a second mode and these ions are ejected from the device in a second, different direction.

8. A method of introducing and ejecting ions from an ion mobility separation device, said method comprising:
   providing an ion entry/exit region having at least two arrays of electrodes;
   temporally separating ions according to a physicochemical property prior to their entry into the ion entry/exit region; then
   receiving the ions in the ion entry/exit region;
   operating the ion entry/exit region in a first mode, wherein DC potentials are successively applied to successive electrodes of at least one of the electrode arrays in a first direction such that a potential barrier moves along the at least one array in the first direction and drives ions into and/or out of the region in the first direction so that the temporally separated ions are ejected from the region in the first direction; and
   temporarily operating the ion entry/exit region in a second mode so as to selectively eject ions having a selected value, or range of values, of said physicochemical property from the region.

9. A method of introducing and ejecting ions from an ion mobility separation device, said method comprising:
   providing an ion entry/exit region having at least two arrays of electrodes;
   operating the ion entry/exit region in a first mode, wherein DC potentials are successively applied to successive electrodes of at least one of the electrode arrays in a first direction such that a potential barrier moves along the at least one array in the first direction and drives ions into and/or out of the region in the first direction;
   ejecting said ions from the ion entry/exit region into an ion guide;
   wherein the ion guide comprises electrodes and the method comprises applying DC voltages to the electrodes of the ion guide so as to drive ions along the longitudinal axis of the ion guide; and
   wherein either a static DC potential gradient is applied along the axial length of the ion guide so as to drive ions along said longitudinal axis; or
   wherein one or more DC potentials is applied to successive electrodes along the axial length of the ion guide such that a DC potential barrier travels along the length of the ion guide and drives ions along the ion guide.

10. The method of claim 9, wherein ions are driven out of the ion entry/exit region, into the ion guide and are then reintroduced back into the ion entry/exit region.

11. The method of claim 10, wherein the potential barrier in the ion entry/exit region urges the reintroduced ions out of the ion entry/exit region again so that the ions and pass through the ion guide again.

12. The method of claim 10, wherein the ions pass through the ion guide≥x times, wherein x is 2, 3, 4, 5, 6, 7, 8, 9, 10, 15 or 20.

13. The method of claim 9, wherein the ion entry/exit region and/or ion guide forms an ion mobility separator in which the ions separate along the longitudinal axis according to their ion mobilities.

14. The method of claim 13, wherein the ions separate according to their ion mobilities as they pass along the ion guide, and wherein the ion entry/exit region is then switched so as to eject at least some of the separated ions out of the device into a further ion guide, ion trap, or ion processing device.

15. The method of claim 14, wherein the ion entry/exit region is temporarily switched such that only ions of a first ion mobility, or first range of ion mobilities, that have passed along the ion guide are ejected out of the ion entry/exit region, whilst other ions having a second ion mobility, or second range of ion mobilities, continue on to pass through the ion guide again.

16. The method of claim 14, wherein the selectively ejected ions are stored, mass analysed, fragmented to form fragment ions, or reacted with ions or molecules to form product ions within said further ion guide, ion trap, or ion processing device.

17. The method of claim 14, comprising reintroducing the selectively ejected ions, fragment ions or product ions into the ion entry/exit region such that the reintroduced ions pass into the ion guide again.

* * * * *